(12) United States Patent
Mastwijk et al.

(10) Patent No.: US 6,178,880 B1
(45) Date of Patent: Jan. 30, 2001

(54) INTEGRATED MODULAR DESIGN OF A PULSED ELECTRICAL FIELD TREATMENT CHAMBER

(75) Inventors: Hendrikus Cornelis Mastwijk, Bilthoven; Paul Vincent Bartels, Wageningen, both of (NL)

(73) Assignee: Instituut voor Agrotechnologisch Onderzoek (ATO-DLO), Wageningen (NL)

(*) Notice: Under 35 U.S.C. 154(b), the term of this patent shall be extended for 0 days.

(21) Appl. No.: 09/438,946

(22) Filed: Nov. 12, 1999

(30) Foreign Application Priority Data

Nov. 11, 1998 (NL) .................................................. 1010529

(51) Int. Cl.[7] .................. A23L 3/00; A23L 3/12; A23L 3/26; A23L 3/32
(52) U.S. Cl. .................. 99/451; 99/358; 99/483; 99/DIG. 14
(58) Field of Search ............... 99/451, 483, DIG. 14, 99/516, 536, 358; 426/234, 237, 238, 410, 407, 241, 247, 248, 521; 422/22–24; 219/700, 779, 735, 771, 780; 392/338, 497

(56) References Cited

U.S. PATENT DOCUMENTS

| | | |
|---|---|---|
| 3,679,556 | 7/1972 | Doevenspeck. |
| 4,695,472 | 9/1987 | Dunn et al.. |
| 5,031,521 * | 7/1991 | Gishko et al. ............... 99/483 X |
| 5,048,404 * | 9/1991 | Bushnell et al. ............... 99/451 |
| 5,235,905 * | 8/1993 | Bushnell et al. ............... 99/451 |
| 5,447,733 * | 9/1995 | Bushnell et al. ............... 426/237 |
| 5,514,391 | 5/1996 | Bushnell et al.. |
| 5,662,031 * | 9/1997 | Qin et al. ............... 99/451 |
| 5,690,978 * | 11/1997 | Yin et al. ............... 426/237 |
| 5,834,746 * | 11/1998 | Pedersen et al. ............... 99/358 X |

OTHER PUBLICATIONS

B.-L. Qin et al., "Inactivating Microorganisms Using a Pulsed Electric Field Continuous Treatment System", IEEE Transactions on Industry Applications, vol. 34, No. 1, Jan./Feb. 1998, pp. 43–49.

* cited by examiner

Primary Examiner—Timothy F. Simone
(74) Attorney, Agent, or Firm—Young & Thompson

(57) ABSTRACT

System for treating pumpable products by electrical pulses comprising at least one treatment chamber formed by at least two modules and comprising a flow channel through which product can be pumped, an end electrode at the one end of the treatment chamber to which a low voltage has to be applied, another end electrode at the other end of the chamber to which a high voltage has to be applied, a generator circuit for generating voltage pulses to be applied to said electrodes. The treatment chamber is provided with at least one intermediate electrode which is located in between the end electrodes and to which a voltage in between the voltages of the two end electrodes has to be applied.

3 Claims, 2 Drawing Sheets

$A = \pi r^2$ $A = \pi r^2$ $A = \pi r^2$ $A = \pi r^2$

INTEGRATED MODULAR DESIGN OF A PULSED ELECTRICAL FIELD TREATMENT CHAMBER

FIELD OF THE INVENTION

The invention relates to a treatment chamber in which a homogeneous pulsed electrical field is generated inside a pumpable product. This product is pumped continuously through the chamber in which a treatment is performed. Application of so-called pulsed electrical field treatment is used as a mild preservation method for foodstuffs and pharmaceuticals, In addition to preservation it also can be used to invoke pores in membranes of cellular structures to promote the transport of (macro-) molecular components across the membrane.

BACKGROUND OF THE INVENTION

The application, process description and several embodiments of so-called pulsed electrical field (PEF) treatment chambers for mild preservation have been discussed in literature. Examples can be found in U.S. Pat. Nos. 5,690,978, 5,662,031, 5,447,733, 5,235,905 and DE-3.708.775. The treatment can be performed by pumping the product through a chamber in which an intense pulsed electrical field is generated. In case treatment is applied as a mild preservation method it seems that most vegetative micro organisms (bacteria, yeasts and fungi) are inactivated at a level of typically 30 kV/cm at temperatures that are less than required in a conventional heat pasteurization process. After treatment the organisms have been found not to reproduce. The total time of a treatment depends on the pulse duration and shape, the total number of impulses tat are applied during the residence time in the treatment zone and the volume flow rate of product through the chamber. In order to achieve a sufficient intense field strength temporarily, high voltage pulses of typically microsecond duration are generated in an auxiliary electronic pulse generating system.

The total duration of the treatment is typical in the range of 10–300 microseconds and depends on the specific application. When electrical pulse treatment is performed as a mild preservation method the required reduction of microbiological counts, the type of product and the specific contamination have to be considered, It is preferred to apply several pulses within the treatment zone. High electrical fields should be imposed typically for a total duration in the range of 2 to 200 microseconds. For other field of applications of a treatment, as e.g. the enhancement of induced mass transport through biological membranes by electroporation, the required electrical field strength is in general less than 30 kV/cm.

The electrical fields are imposed to the product using an electrode structure to which high voltage pulses are applied. The electrodes are in physical contact with the product and are contained in a mechanical construction through which the product is pumped. The combination of the electrodes, electrically isolating holders and sealing is referred to as treatment chamber. When produce is pumped through this chamber a treatment is performed in the resident period by applying short high voltage pulses to the electrodes at a sufficiently high rate.

SUMMARY OF THE INVENTION

In this specification a system is considered where a product is pumped through a treatment chamber and where a stationary state in product flow and temperature is reached. In principle, no stationary conditions can be met since pulses are repeatedly applied in the process. However, the energy input by the short electrical pulses can be time averaged. In practice steady state flow and temperature conditions can be reached. In this discussion $\phi$ is denoted as the volume flow rate of the product and V the effective volume of the treatment chamber. The average residence time t of a fluid element in the device is given by $t=V/\phi$. In this time the pulse treatment takes place. The required electrical peak power in treatment is given by $Pp=\sigma E^2 V$, where V denoted the effective volume of the treatment chamber, $\sigma$ the mean product conductivity and E the average of the electrical field strength across the treatment device. The mean consumed electrical power is given by the relation $Pc=\sigma E^2 \tau \phi$ where $\tau$ is the total treatment time of a fluid element. The latter is the total duration tat a high electrical field is imposed on the transversing product. In case that square wave pulses are used with a duration $\tau_p$ the total treatment time is defined as $\tau=N^*\tau_p$ with N the mean number of pulses applied on the product when resident in the chamber.

The electrical energy is converted into heat inside the product due to Ohmic heating. In general the temperature increase during treatment can be kept below 30 degrees centigrade. However, a small temperature increment results in a strong increase in electrical conductivity of the product. This is known to be the case for many different solutions containing minerals and for foodstuffs in particular. As an illustration: the electrical conductivity of a 0.75% KCl solution increases by more than 15% in the temperature range of 18–25 degrees centigrade (CRC, Handbook of Chemistry and Physics, $72^{nd}$ edition, 1991–1992).

The required peak power for a treatment of a column of product with length L and cross-section A is given by $P=\sigma E^2 AL=\sigma E^2 V$ in case a homogeneous electrical field distribution is assumed. For a column of product of conductivity $\sigma$ in which an electrical field is present with the direction along its length, the ohmic resistance is given by $R=L/\sigma A$. In general only die real part of the electrical impedance is of importance. The parasitic capacity and self-inductance in a column of product is therefore neglected in this discussion.

The geometry of the treatment chamber determines the largest possible size and shape of a channel through which the product can flow. In principle the size and shape of the channel should be such that the flow resistance is minimised. The magnitude of the electrical field strength and the uniformity of the electrical field distribution are not only determined by the dimensions of the chamber. Also the distribution of the electrical conductivity of He product across the treatment chamber should be considered.

When a local current density of magnitude j is generated in a fluid element of electrical conductivity $\sigma$, an electrical field of strength E across the element is imposed. Its magnitude is given by $j=\sigma E$ (Ohms law). In practice it is important that all fluid elements that are pumped through a treatment chamber should receive a minimal treatment. That is, both the treatment time and the magnitude of the applied electrical field should be sufficiently high. The design of the treatment device and the electrode configuration determine how the electrical field strength is distributed in tie product stream. It is preferred to create a uniform electrical field distribution across the treatment zone.

In U.S. Pat. No. 5,235,905 a coaxial treatment device is considered. A major disadvantage of this design is the limited width of the annulus trough which the product can flow. In addition it has relatively large electrode surfaces.

U.S. Pat. No. 5,690,978 describes a co-linear treatment chamber. A disadvantage of the latter is its non-uniform distribution of the electrical field in the treatment zone. For a fixed diameter of this type of chamber a so-called gap distance has to be chosen. In case small gap distances (with respect to the diameter) are considered the electrical field distribution at the entrance and exit of the treatment zone is highly non-uniform. In case the gap distance is enlarged the non-uniformity in the field distribution is of less importance. However, in a treatment chamber with a large gap distance a fairly large temperature gradient will appear across the treatment zone at steady state conditions. This has a negative impact on the electrical field distribution across the fluid column inside the chamber. This is related to the fact that the electrical conductivity of products and solutions containing minerals in general are temperature dependent. The electrical conductivity for these products increases at higher temperatures. Due to the heat production in the chamber when receiving pulse treatment the temperature of the product at the exit of the treatment zone becomes higher than at the entrance. This leads to the built up of a gradient in the electrical conductivity across the treatment zone. As a result the voltage drop over the product column will change. This results in a smaller electrical field in the region near the exit of the treatment zone. The electrical field strength near the entrance will be higher. This treatment is however, over a much smaller region of the chamber volume and therefore lasts for a shorter period of time. As a result the spread in the effective field strength and spread in the treatment time in the product increases. This has an adverse affect on for example the degree of microbiological inactivation. In addition to this temperature induced effect the release of minerals and other components by cellular membrane structures will cause a similar effect. This can lead to a change in conductivity in the product across the treatment zone (for example: due to electroporation of biological membranes intracellular contents can be released).

In U.S. Pat. No. 5,690,978 the above-mentioned problem on die change of electrical conductivity over a product column is not recognized. However, tis issue is of major importance as the direction of the electrical field strength is parallel to the flow direction and hence to a gradient in the electrical conductivity. In U.S. Pat. No. 5,690,978 an extension of the number of treatment clambers in series is mentioned. The temperature increment across each individual treatment chamber in this system is of less importance. This is certainly the case when intermediate cooling is applied to remove the heat deposited in the product after each treatment. However, by increasing the number of treatment chambers with a small electrode gap distance the non-uniformity of the electrical field distribution remains.

In this specification a novel modular design of a PEF treatment chamber is described comprising an open electrode structure with a large aperture. In this design the problem of non-uniformity due to a gradient in the product conductivity at steady state flow conditions is solved. The treatment chamber consists of several identical modules. Each module has a large aperture yet a small internal volume. By proper positioning of several of these modules the non-uniformity in the electrical field distribution of individual modules is compensated. As a result the overall electrical field strength of the treatment camber is uniform across the volume. As tie different modules contain electrodes that can be connected to a certain voltage, the electrical field strength in all modules can be imposed individually.

DETAILED DESCRIPTION OF THE INVENTION

Figure 1:
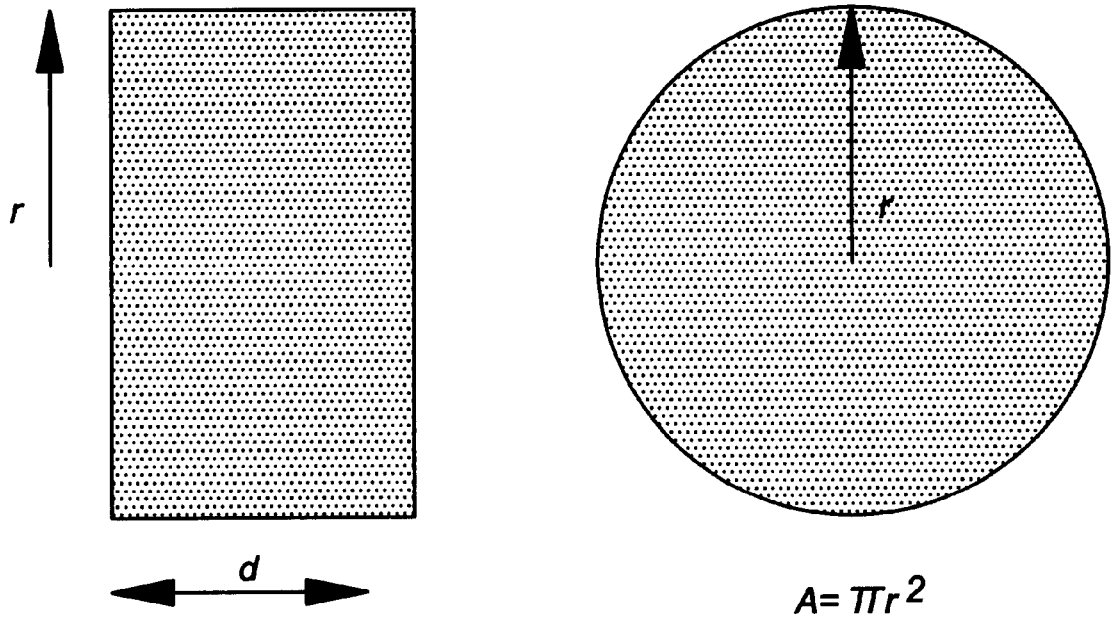
FIG. 1 depicts a cylindrical column of fluid.
Figure 2:
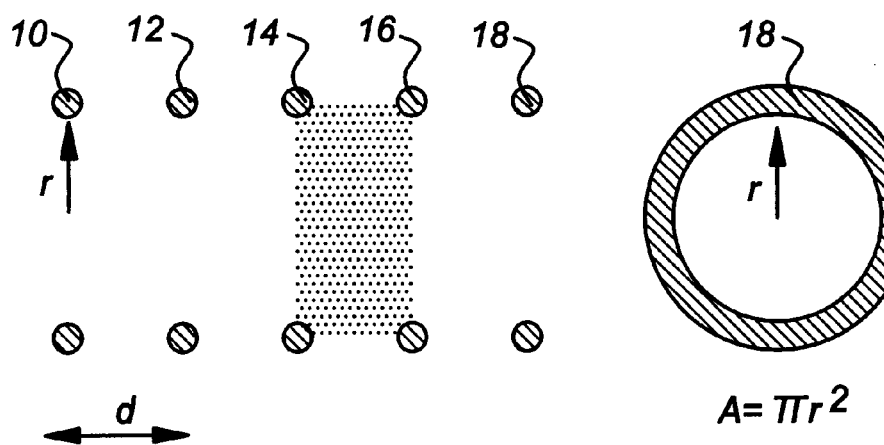
FIG. 2 depicts an electrode configuration having a suitable aperture for pumping a product therethrough while imposing a uniform electrical field distribution.
Figure 3:
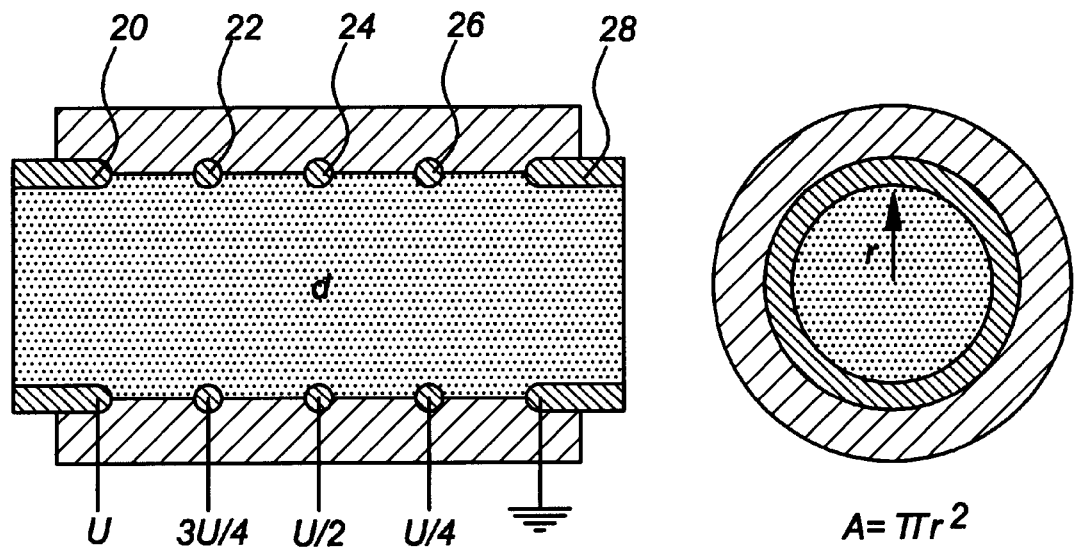
FIGS. 3 and 4 depict treatment chambers embodying the electron configuration of the present invention.

In general, for a given configuration of electrodes the electrical field can be found at every point by solving Laplace's equation for the given boundary conditions. The problem may include a gradient in conductivity. At this point a column of fluid (product) is considered of cylindrical cross section (FIG. 1). Different cross-sectional shapes give similar results. An electrode configuration that both has a suitable aperture through which product can be pumped and imposes a uniform electrical field distribution at the same time, is depicted in FIGS. 2 and 3. This configuration consists of a sequence of modules (separated by a distance d and with cross-sectional area A) with a geometric volume V given by V=d*A. The boundaries of these modules are enclosed by circular shaped equipotentials. It has turned out that although the electrical field distribution of a single module is not uniform. However, in case that an array of properly coupled modules is considered a uniform field is obtained over the volume of each module.

As mentioned the boundaries of each module should be fixed to a circular equipotential. This requirement can be met by introducing circular shaped electrodes as depicted in FIGS. 2 and 3.

The voltage difference of the electrodes at the sides of the i-th module is given by Vi=E*d. The current density in the i-th cell of the array is given by $j_i=\sigma_i E$. Note that the current density in successive cells can vary and dependant on the conductivity of the product is the i-th cel, The total electrical current in the i-th cell is given by $I_i=j_i A$. The electronic impedance of the i-th cell is given by $Ri=d/\sigma_i A$. If the voltage difference at the electrodes of successive modules increases by an amount on E*d, a uniform electrical field is obtained in the entire internal volume of the array.

The required electrical peak power of the i-th cell is given by $Pp,i=\sigma_i E^2 Ad$. The continuous power consumption by the i-th cell is given by $Pc,i=\sigma_i E^2 \tau\phi$. By variation of voltage on the annular electrodes the electrical field in the i-th cell can be imposed electronically. To achieve a uniform electrical field across the treatment chamber, the voltage difference of successive annular electrodes is given by E*d. The total potential difference (Ut) across the treatment chamber is Ut=(n−1)*E*d, in case n electrodes are used.

It should be noted hat a uniform field across the array may also be obtained by changing the spacing di and cross-sectional area Ai of successive cells. Although the relative voltages on die electrodes may change the principle design of the treatment chamber remains the same. Apart from a uniform electrical field, an increasing or decreasing field strength across the treatment chamber can be obtained. In general the voltages Ui imposed on the i-th electrode can be arbitrary as well as the distances di and cross-sections Ai.

In the design of a practical treatment chamber a choice has to be made for the number of modules that is required, the radius of the electrodes and the separation distances. The radius of the electrode primarily depends on the minimum required cross-sectional area. This in turn depends on the required throughput of and the reological properties of the product. The choice in the number of modules and the separation distances of the electrodes depend on the electrical properties of the product, the required field strength and total treatment time. The total length of the treatment chamber is preferentially large in comparison to the radius of the circular electrodes. The electrical field distribution of the first and the last cell are slightly non-uniform. This is due to the fact that translation symmetry in the electrode array is absent.

Figure 4:
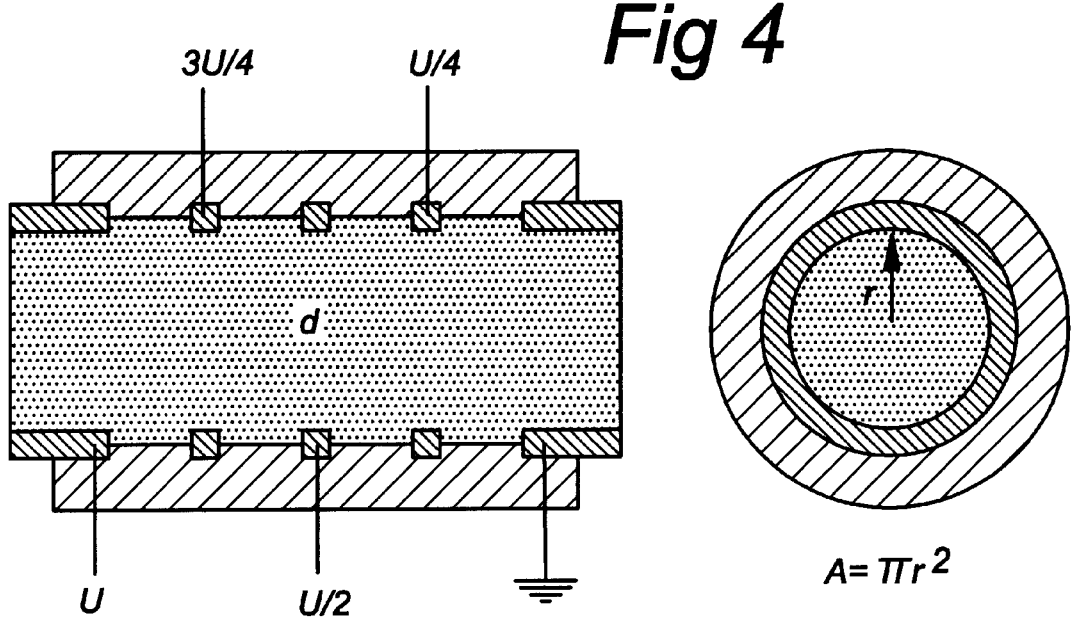

Examples of two practical designs of the above described treatment chamber are shown in FIG. 3 and 4. The treatment chambers have cylindrical cross-sections and consist of 4 modules using 3 annular electrodes. The electrodes are spaced by electrical insulating material and contain the annular electrodes. The electrical connections of the electrode outward are not shown. The flow of product is in the direction of the imposed electrical field or head on to the electrical field depending on the choice of voltages. In this example at the most left electrode a pulsed voltage of magnitude U is used. The voltage at the successive electrodes gradually decreases towards the right side. At the left-hand side and the right-hand side the electrode array is connected to a tube. This tube may be part of an auxiliary fluid handling system. In this example the tubes are assumed to be of metal with high electrical conductivity and act as an anode and cathode. When using circular electrodes with a circular cross-section (FIG. 4) the risk of Corona emission due to local field maxima at the insulator-electrode-product interfaces is reduced.

Advantages

The advantages of the treatment chamber described in this patent are

- The aperture of each module has a large cross sectional area with respect to the contained volume
- The electrical field distribution is uniform even when a gradient in conductivity across the treatment device is present
- The construction of the treatment device is simple and can be easily cleaned.

Due to its design the peak power that is needed can be distributed over several modules which can be fed by different auxiliary pulse power supplies

What is claimed is:

1. Apparatus for treating pumpable products by electrical pulses, comprising:

at least one treatment chamber formed by at least two modules, and having a first end and an opposite second end, and a flow channel extending between said ends for pumping a product therethrough;

a first end electrode at said first end, and means for applying a first voltage to said first end electrode;

a second end electrode at said second end, and means for applying a second voltage to said second end electrode, said first voltage being lower than said second voltage;

a generator circuit for generating voltage pulses to be applied to said electrode; and at least one intermediate electrode positioned between said end electrodes, and means for applying a third voltage to said intermediate electrode, said third voltage having a level between said first voltage and said second voltage.

2. The apparatus according to claim 1, wherein the treatment chamber comprises n intermediate electrodes positioned in succession between said end electrodes, and means for applying a level of voltage to each successive electrode, such that the voltage level of an intermediate electrode lies between the voltage of two neighboring electrodes.

3. The apparatus according to claim 2, wherein the mutual distances between successive electrodes are substantially equal, and the voltages applied to successive electrodes are defined as $0, U/(n+1), 2*U/(n+1), \ldots, n*U/(n+1), U$, wherein n is the number of electrodes, and U is the potential difference.

* * * * *